(12) United States Patent
Swietoslawski et al.

(10) Patent No.: US 11,464,224 B2
(45) Date of Patent: Oct. 11, 2022

(54) LIQUID SPREADING COMPOSITION WITH ECTOPARASITICIDAL ACTIVITY, A METHOD AND USE THEREOF FOR COMBATING ECTOPARASITES IN HUMAN AND VETERINARY MEDICINE, AS WELL AS IN AGRICULTURAL, HORTICULTURAL AND/OR GARDEN ENVIRONMENTS

(71) Applicant: ICB Pharma Spolka Jawna, Jaworzno (PL)

(72) Inventors: Janusz Swietoslawski, Jaworzno (PL); Anna Gawron, Brzeszcze (PL); Dawid Liszka, Jaworzno (PL)

(73) Assignee: ICB PHARMA SPOLKA JAWNA, Jaworzno (PL)

( * ) Notice: Subject to any disclaimer, the term of this patent is extended or adjusted under 35 U.S.C. 154(b) by 85 days.

(21) Appl. No.: 15/500,502

(22) PCT Filed: Jul. 30, 2014

(86) PCT No.: PCT/PL2014/000090
§ 371 (c)(1),
(2) Date: Jan. 30, 2017

(87) PCT Pub. No.: WO2016/018164
PCT Pub. Date: Feb. 4, 2016

(65) Prior Publication Data
US 2018/0035662 A1    Feb. 8, 2018

(51) Int. Cl.
| A01N 25/02 | (2006.01) |
| A01N 25/06 | (2006.01) |
| A01N 37/02 | (2006.01) |
| A01N 27/00 | (2006.01) |
| A01N 31/14 | (2006.01) |
| A01N 37/36 | (2006.01) |

(52) U.S. Cl.
CPC ............. *A01N 25/02* (2013.01); *A01N 25/06* (2013.01); *A01N 27/00* (2013.01); *A01N 31/14* (2013.01); *A01N 37/02* (2013.01); *A01N 37/36* (2013.01)

(58) Field of Classification Search
CPC ........ A01N 37/02; A01N 43/40; A01N 27/00; A01N 25/06; A01N 25/02; A01N 31/14; A01N 37/36; A61P 33/10; A61P 33/14
See application file for complete search history.

(56) References Cited

U.S. PATENT DOCUMENTS

| 4,147,800 | A | 4/1979 | Singer et al. | |
| 4,626,274 | A | 12/1986 | Hausmann et al. | |
| 6,663,876 | B2 | 12/2003 | Campbell et al. | |
| 8,178,116 | B2 * | 5/2012 | Campbell | A01N 37/02 424/405 |
| 8,388,986 | B2 * | 3/2013 | Urgell Beltran | A61K 8/44 424/401 |
| 2009/0123398 | A1 * | 5/2009 | Laba | A61K 8/31 424/59 |
| 2011/0265810 | A1 * | 11/2011 | Pelusi | A45D 7/06 132/206 |
| 2012/0029025 | A1 | 2/2012 | Nouvel | |
| 2013/0018016 | A1 | 1/2013 | Ueck | |
| 2013/0072455 | A1 | 3/2013 | Campbell et al. | |
| 2013/0149272 | A1 * | 6/2013 | Hloucha | A61K 8/068 424/70.13 |

FOREIGN PATENT DOCUMENTS

| CN | 101642093 | | 2/2010 | |
| CN | 102836094 | | 12/2012 | |
| EP | 0191543 | | 8/1986 | |
| GB | 1604853 | | 12/1981 | |
| GB | 2204243 | A | 11/1988 | |
| WO | WO-9214459 | A2 * | 9/1992 | ............ C07F 9/6533 |
| WO | 200072814 | A1 | 7/2000 | |
| WO | 200071093 | A1 | 11/2000 | |
| WO | WO-0072814 | A1 * | 12/2000 | ............. A61Q 17/02 |

(Continued)

OTHER PUBLICATIONS

International Preliminary Report on Patentability; PCT/PL2014/000090; Filed Jul. 30, 2014.
International Search Report; PCT/PL2014/000090; Filed Jul. 30, 2014.
Written Opinion of the International Searching Authority; PCT/PL2014/000090; Filed Jul. 30, 2014.
Hair Oil Essence Deep Repair—Product Description; Global New Products Database; Jun. 1, 2007 (Jun. 1, 2007), pp. 1-2, XP055152216, U.K., Retrieved from the Internet: URL: www.gnpd.com [retrieved on Nov. 11, 2014] ingredients.
Light Texture Paste—Product Description; Global New Products Database; May 1, 2009 (May 1, 2009), pp. 1-2, XP055152220, U.K., Retrieved from the Internet: URL: www.gnpd.com [retrieved on Nov. 11, 2014] ingredients.

(Continued)

*Primary Examiner* — Jean P Cornet
(74) *Attorney, Agent, or Firm* — Ware, Fressola, Maguire & Barber LLP

(57) ABSTRACT

The present invention relates to a liquid spreading composition with ectoparasiticidal activity. The invention also relates to a method and use of such a liquid spreading composition for combating ectoparasites in human and veterinary medicine, as well as in agricultural, horticultural and/or garden environments. The composition comprises at least one emollient ester and isohexadecane, wherein the weight ratio of said at least one emollient ester to isohexadecane is within 1:9 to 7:3. The invention improves the spreading properties of a composition enabling it for an efficient delivery of an active substance or substances over the surface of the host on which it is applied. The spreading composition may also be used alone for an efficient ectoparasiticidal treatment in human and veterinary medicine, as well as for combating ectoparasites in agricultural, horticultural and/or garden environments. With at least one additional agent the spreading composition may also be used in cosmetic, as well as for pest control, including insect and rodent control.

4 Claims, No Drawings

(56) References Cited

FOREIGN PATENT DOCUMENTS

| WO | 0119190 | 3/2001 |
|---|---|---|
| WO | 2003092583 A2 | 11/2003 |
| WO | 2005027636 | 3/2005 |
| WO | 2010031584 | 3/2010 |
| WO | 2011009617 | 1/2011 |
| WO | 2011103694 A1 | 1/2011 |
| WO | 2013140367 | 9/2013 |
| WO | 2016018164 A1 | 4/2016 |

OTHER PUBLICATIONS

Sun-Protection Sealing Fluid—Product Description; Global New Products Database; Jul. 1, 2005 (Jul. 1, 2005), pp. 1-2, XP055152221, U.K., Retrieved from the Internet: URL: www.gnpd.com [retrieved on Nov. 11, 2014] ingredients.
"Personal Care Product Guide", Croda, Apr. 1, 2010, pp. 1-72.
Didier Raoult, et al., "The Body Louse as a Vector of Reemerging Human Diseases", Clinical Infectious Diseases, vol. 29, No. 4, Oct. 1, 1999, pp. 888-911.

\* cited by examiner

LIQUID SPREADING COMPOSITION WITH ECTOPARASITICIDAL ACTIVITY, A METHOD AND USE THEREOF FOR COMBATING ECTOPARASITES IN HUMAN AND VETERINARY MEDICINE, AS WELL AS IN AGRICULTURAL, HORTICULTURAL AND/OR GARDEN ENVIRONMENTS

The present invention relates to a liquid spreading composition with ectoparasiticidal activity. The invention also relates to a method and use of such a liquid spreading composition for combating ectoparasites in human and veterinary medicine, as well as in agricultural, horticultural and/or garden environments.

BACKGROUND OF THE INVENTION

Various spreading compositions are known from the state of art.

Application US 2012/0029025 A1 for example discloses a spot-on pesticide composition for animals, specifically mammals, including dogs and cats, which composition comprises a combination of active components which are parasiticidally effective against a variety of insects and pests, and in a formulation which is convenient for local application to the animal's skin, preferably localized over a small surface area. Such a spot-on treatment can be applied to the animal in smaller portions, while maintaining treatment efficacy across the entire body surface of the animal.

Spreading compositions are also used for treatment of pediculosis (an infestation by lice) in humans, where they act as a carrier of an insecticidal substance such as pyrethrum extract or synthetic pyrethroids such as permethrin or an organophosphorus insecticide such as malathion. An alternative treatment is based on physical action acting through immobilization and mechanical blockage of the louse's breathing apparatus. An advantage of a treatment of this kind is that ectoparasites are virtually unable to evolutionary develop resistance against the treatment and unlike traditional insecticides, which are frequently even more hazardous than the pediculosis itself, such a treatment has no toxic effects to humans.

The most popular ectoparasiticidal compositions of this kind are based on silicones such as linear siloxanes (e.g. GB 1 604 853), cyclic siloxanes (e.g. EP 0191 543), mixtures thereof (e.g. EP 1 215 965), or mixtures with cyclic siloxanes with vitamin E (e.g. WO 2010/031584) or with fatty acid esters such as isopropyl myristate (e.g. U.S. Pat. Nos. 6,663,876 and 8,178,116) or with isopropyl palmitate (e.g. US 2013/0072455). Silicone based compositions are nonetheless disadvantageous from the hair health point of view, since they form silicone coatings over hair shafts. Such coatings in turn prevent penetration of hair shafts with moisturizing ingredients, essential oils, proteins and other nutritional agents, which results in hair weakness. An extensive amount of silicone products may also lead to the build-up of silicone coatings eventually cause breakages of hair shafts. Finally, a sulfate shampoo and/or cleanser is/are required in order to remove such silicone coating from hairs. This however also makes hairs dry and/or prone to breakage and some persons may be allergic to sulfate shampoos and/or cleansers.

Relatively smaller number of non-silicone based ectoparasiticidal compositions for pediculosis treatment is also known from the state of art. Patent publications U.S. Pat. No. 4,147,800 and WO 2005/027636 (Example 4) disclose compositions containing fatty acid ester with isopropyl alcohol which may leads to adverse reactions such as eye irritation and an unpleasant skin cooling effect when used on animals, especially on cats. Publication U.S. Pat. No. 4,147,800 discloses killing properties of isopropyl myristate in different concentrations: concentration of over 80% by weight provides 100% of mortality of adult lice, whereas concentration below 70% by weight provides less than 20% mortality. U.S. Pat. No. 4,147,800 is silent about efficacy against louse eggs.

Publication US 2013/0018016 A1 discloses a composition for killing ectoparasites and/or their eggs, comprising at least one volatile at room temperature, liquid, non-polar organic solvent, 1 to 10 wt.-%, based on the total composition, of at least one spreading agent and 35 to 65 wt.-%, based on the total composition, of at least one polysiloxane having a viscosity of greater than 90 cSt. As spreading agent the compositions disclosed in US 2013/0018016 A1 may contain medium-chain triglycerides, coconut oil, palm kernel oil, babassu oil, jojoba oil, jojoba wax, cetearyl isononanoate, cetearyl octanoate, isopropyl myristate, isopropyl palmitate, ethylhexyl palmitate, and cocoyl caprylocaprate.

International patent application WO 2013/140367 discloses a composition for the treatment of human or animal pediculosis including at least one first active principle having filmogenic properties and which is designed to cover, at least partially, at least one parasite responsible for said pediculosis, to prevent the latter from breathing, said composition being characterized in that said at least one active principle is encapsulated in at least one globule whose size is designed to allow said globule to penetrate into the breathing orifices of said at least one parasite and its eggs.

Spreading compositions are also used in cosmetic. Publication CN 102836094 A, for example, discloses a self-prepared skin-care cosmetic essential oil of cosmetics as an O/W-type microemulsion, comprising at least one specific polymer, at least one vegetable oil, at least one C12-C20 saturated fatty acid or unsaturated fatty acid, at least one C2-C6 monohydric alkanol ester of lauric acid, ethers of at least one C12-C18 monohydric alcohol or poly(dihydric) alcohol or C1-C18 aliphatic ester derivatives. The self-prepared skin-care cosmetic essential oil has the characteristics of clear and transparent appearance, uniformity and good stability. The essential oil is used as a base material and mixed with water, water-containing medium or alcohols substances according to different proportions to immediately form the cosmetics such as moisturizing creams, massage creams, cleansers, facial mask emulsions or makeup removing lotions and is a simple, instant and multifunctional DIY cosmetic precursor. The prepared cream has the characteristics of good sticking performance, good spreading property on skins, good permeability on skins, no greasy feeling and good moisturizing property.

Various examples of spreading compositions may also be found in agriculture and horticulture. Patent publication U.S. Pat. No. 4,626,274 A, for example discloses a combination of a known herbicide such as a urea, carboxylic acid ester, amino acid, benzoic acid derivative, benzonitrile, phenol derivative, diphenyl ether, carbamate, phenoxyalkanecarboxylic acid, triazine, triazinone, triazinedione, heterocycle, dipyridil derivative or benzosulphonamide, with a synthetic spreading agent such as a silicone oil, fatty acid ester or fatty alcohol, e.g. isopropyl myristate, metamitron, ametridion or methabenzthiazuran. Such a combination renders this known herbicide to be more effective. Patent publication CN 101642093 A discloses a botanical pesticide solvent, in particular to a pesticide solvent taking vegetable oil and co-solvent as raw materials. Said solvent contains 85% to 100% of vegetable oil and 0% to 15% of co-solvent in percentage by weight; the vegetable oil is at least one of jatropha curcas oil methyl ester and jatropha curcas oil. The co-solvent is at least one of isopropanol, glycol, N-methylpyrrolidone, N-ethyl pyrrolidone, N-octyl pyrrolidone and azone. Disclosed botanical pesticide solvent has good spreading permeability and is suitable for preparing various kinds of pesticide ingredients such as insecticide, acaricide, bactericide, weedicide and plant growth regulator and the like.

Therefore, the term "spreading composition" as used in the context of the present application means a composition that after being applied in small amount at some spot of a surface, and in particular plant covering or animal, including human, skin is capable of spreading over the surface around this spot, in particular as a thin layer having surface area significantly greater than the spot area.

It has been the object of the present invention to provide a spreading composition featuring spreading properties which are superior to the compositions known from the state of art. Such a composition might in turn be applied for an efficient delivery of various substances including various active substances over the surface of the host on which it is applied.

Another object of the present invention has been to provide a spreading composition that might be used for an efficient ectoparasiticidal treatment in human and veterinary medicine, as well as for combating ectoparasites in agricultural, horticultural and/or garden environments.

SUMMARY OF THE INVENTION

According to the present invention there is provided a liquid spreading composition with ectoparasiticidal activity, characterized in that it comprises at least one emollient ester and isohexadecane, wherein the weight ratio of said at least one emollient ester to isohexadecane is within 1:9 to 7:3.

The inventors worked on improving spreading characteristics of known liquid compositions, in particular those applied to skin and/or hair of mammals. During tests of various combinations of emollients (in particular cosmetic emollients) used as carriers for different known active ectoparasiticidal agents, it has been unexpectedly discovered that combination of at least one emollient ester and isohexadecane features surprising synergistic effect with regard to its spreading value. This in turn enabled for up to c.a. 2 to 10 fold lower application dose as compared to known spreading compositions as shall be described later (cf. Table 1).

Isohexadecane (CAS No. 93685-80-4) is branched chain hydrocarbon with 16 atoms. Isohexadecane is also commonly used as emollient, skin conditioning agent and solvent in substantially dense personal care products such as creams, mascaras, lipsticks, etc. Owing to the high isohexadecane boiling temperature of about 240° C., it does not produce an unpleasant skin cooling effect that is a disadvantage of known ectoparasiticidal compositions when used on animals, especially on cats.

Furthermore, the composition of the present invention does not contain silicone. Therefore it is relatively easy to remove from the surface that it has been spread over and may be successfully employed as a carrier for various active substances in particular in human and veterinary medicine, agricultural, horticultural and/or garden environments, cosmetic, as well as in pest control including insect and rodent control.

Preferably said at least one emollient ester is a fatty acid ester.

Preferably said fatty acid ester is selected from the group including: myristate, laureate, palmitate, stearate, arachidate, pamitolate, oleate, linoleate, linolenate, and arachidonate.

More preferably said fatty acid ester esters according to the present invention include isopropyl esters, methyl esters, ethyl esters and propyl esters that are commonly used as emollients in cosmetic products.

Yet more preferably said fatty acid ester esters are selected from the group including: isopropyl myristate or isopropyl palmitate, and even more preferably said fatty acid ester is isopropyl myristate.

The fatty acid esters that are particularly useful according to the present invention are also esters of C1-C4 alcohols.

Preferably the composition comprises at least one surfactant, preferably in an amount of up to 10% by weight.

Surfactants facilitate the wash up of the composition from the covered surface such as hair and scalp by creating O/W emulsion. Preferred surfactants are surfactants approved for use in cosmetic products. Most preferred surfactants are: polyethylene glycol (40) sorbitol oleate, polyethylene glycol (30) hydroxystearate, polyethylene glycol (20) sorbitol oleate or 1,2-octanediol (capryl glycol).

The composition of the present invention may additionally comprise at least one additional agent preferably selected from the group including: an inert pharmaceutically or cosmetically acceptable carrier, fragrance, insecticide, insect growth regulator such as (S)-methoprene or pyriproxyfen and/or adulticide such as permethrin, d-phenothrin or essential oils.

It has also been discovered that the composition of the present invention can be used alone as an insecticidal formulation for controlling ectoparasites on mammals, in particular as a spot-on or pour-on type.

Accordingly the invention provides an insecticide composition, in particular an ectoparasiticidal composition, comprising the liquid spreading composition defined above.

The present invention also provides a method of treating ectoparasite infestation in a host comprising topically applying to the host an effective amount of the liquid spreading composition with ectoparasiticidal activity as defined above.

Preferably said host is a plant, an animal or a human. Preferably said ectoparasites are selected from the group including: lice, ticks and fleas.

Most invertebrates breathe using an open respiratory system by exchanging gas through openings in the surface of the body. The system is usually composed of spiracles, tracheae, and tracheoles, branching internal tubes that run from these openings and deliver oxygen directly to individual cells of the animal. Furthermore many insect species have spiracles provided with an actively tight-closing valvule apparatuses preventing against loss of water from the insect body interior. Insect takes in oxygen while it is active and small amounts of carbon dioxide are released when the insect is at rest.

The composition according to the present invention forms a molecular three-dimensional matrix all over an ectoparasite body what results in immobilization of the ectoparasite.

Furthermore, it has been discovered that due to very low surface tension the composition remarkably well penetrates the ectoparasite surface including interior of spiracles, tracheae that are generally protected by hairs and other structures preventing against entering impurities. After penetration valvule apparatuses are also immobilized. If a valvule is immobilized in a closed state then the spiracle trachea is no longer supplied with oxygen and the insect tissue connected with the spiracle trachea is mortified. On the other hand a valvule immobilized in an opened state lead to insect dehydration.

Therefore the invention provides use of a composition defined above, alone or comprising at least one additional agent for combating ectoparasites in human and veterinary medicine, as well as in agricultural, horticultural and/or garden environments.

Finally the invention provides use of a composition defined above comprising at least one cosmetically acceptable additional agent in cosmetic, as well as use of a composition defined above comprising at least one pest controlling agent in for pest control including insect and rodent control. Various additional active substances that may be used for these purposes are known to those skilled in the art.

When used as a carrier for other agents having toxic activity against pests including ectoparasites, spreading composition of the present invention also provides synergistic effects:
- it enhances effects of a toxic agent by changing the "exposure profile", as well as by increasing efficiency by additional mechanism of action, what results in synergistically summing the action of pest controlling agents with effects of the composition alone (e.g. neurotoxic action and mechanical action);
- it increases a proliferative potential (surface covering) of a toxic agent used in the mixture with the inventive spreading composition, providing an excellent penetration of the surface sprayed with the composition, which is important in particularly in combating species inhabiting poor access locations, such as for example bed bug or common clothes moth;
- it emulsifies specific hydrocarbons constituting components of cuticle covering the body of an insect; damage of this continuous external ceraceous protective covering also results in a change in the "exposure profile" of an insect, so that the insect is more susceptible for the action of the toxic agent that penetrates inside the insect in greater concentration;
- it immobilizes an insect making it permanently exposed to the influence of the toxic agent (if any) and the composition alone.

DETAILED DESCRIPTION OF THE INVENTION

Without further elaboration, it is believed that one skilled in the art can, using the preceding description, utilize the present invention to its fullest extent. The following preferred specific embodiments and tests are, therefore, to be construed as merely illustrative, and not limitative of the remainder of the disclosure in any way whatsoever.

Example 1

A composition of the present invention has been prepared containing:
- isopropyl myristate (IPM) in the amount of 50% by weight;
- isohexadecane in the amount of 48% by weight;
- polyoxyethylene (40) sorbitol oleate in the amount of 1.8% by weight; and
- fragrance in the amount of 0.2% by weight.

Spreading Tests

The following tests have been performed to measure and compare spreading properties of the composition prepared according to Example 1 (N) with Isopropyl Myristate (IPM) and Diethylene Glycol Monoethyl Ether (DGME), known from the state of art as spreading agents. All compositions acted as a carrier of an active insecticidal substance: clove oil (an insect repellent), S-Methoprene (biochemical pesticide interfering with an insect's lifecycle and preventing it from reaching maturity or reproducing) or Etofenprox (neurotoxic insecticide, which disturbs insect nervous systems).

Table I shows the results of these tests were performed by applying 5 µl drop of the composition in the middle of a glass plate at 25° C. Area (S) of the surface ($cm^2$) covered by the composition has been measured after 30 min. As an alternative spreading indicator one might also employ Emollient Skin Spreading Factor as defined by Croda (Croda DS-128, Emollient Skin Spreading Factor (1998)).

TABLE I

Spreading properties of compositions acting as active substance carriers

| Comp. No. | Main ingredients (volume fraction [%] or mass fraction [% by weight]) | S [$cm^2$] 5 µl/30 min glass surface |
|---|---|---|
| 1. | Clove oil (20%) + IPM (80%) | 0.6 |
| 2. | Clove oil (20%) + DGME (80%) | 0.6 |
| 3. | Clove oil (20%) + N (80%) | 12.0 |
| 4. | S-Methoprene (10%) + IPM (90%) | 0.6 |
| 5. | S-Methoprene (10%) + DGME (90%) | 0.7 |
| 6. | S-Methoprene (10%) + N (90%) | 22.0 |
| 7. | Etofenprox (40% by weight) + IPM (60% by weight) | 0.6 |
| 8. | Etofenprox (40% by weight) + DGME (60% by weight) | 0.5 |
| 9. | Etofenprox (40% by weight) + N (60% by weight) | 7.0 |
| 10. | IPM (100% by weight) | 0.6 |
| 11. | DGME (100% by weight) | 0.6 |

Test results in Table I clearly indicate excellent spreading features of the composition of the present invention which in each case significantly increased the area available for delivery of an active substance.

The following tests have been performed to measure and compare spreading properties of the composition prepared according to Example 1 with ectoparasiticidal compositions known from the state of art. As in the previous tests 5 µl drop of the composition has been applied in the middle of a glass plate at 25° C. Area of the surface ($cm^2$) covered by the composition has been measured after 30 min.

TABLE II

Spreading properties of the composition according to the invention compared to known ectoparasiticidal compositions (pediculosis treatment)

| Composition (Manufacturer/ Distributor) | Main ingredients (volume fraction [%] or mass fraction [% by weight]) | S [$cm^2$] 5 µl/30 min glass surface |
|---|---|---|
| Composition of the invention (Example 1) | IPM (50% by weight) + isohexadecane (48% by weight) | 46.6 |
| Nyda spray (Siroscan) | Dimethicone (92%) | 3.5 |
| Hedrin 4% lotion dimeticone (Thornton& Ross) | cyclomethicone D5 (96%) + dimethicone (4%) | 2.8 |
| Hedrin Treat&Go lotion (Thornton& Ross) | Octane-1,2-diol + PEG-6 caprylic/ capric glycerides + $H_2O$ | 2.3 |
| Hedrin Treat&Go spray (Thornton& Ross) | Octane-1,2-diol + PEG-6 caprylic/ capric glycerides + $H_2O$ | 2.0 |

TABLE II-continued

Spreading properties of the composition according to the invention compared to known ectoparasiticidal compositions (pediculosis treatment)

| Composition (Manufacturer/ Distributor) | Main ingredients (volume fraction [%] or mass fraction [% by weight]) | S [cm$^2$] 5 μl/30 min glass surface |
|---|---|---|
| Hedrin Once Spray Gel (Solpharm) | Dimethicone + PEG/PPG dimethicone-co-polymer + SiO$_2$ | 1.3 |
| Lyclear spray (Chefaro) | Mineral oil + dimethicone | 1.3 |
| Paranit (Medgenix) | Mineral oil surfactant | 0.3 |

Test results in Table II clearly also indicate excellent spreading features of the composition according the present invention.

Ectoparasiticidal Tests

During further research the inventors tested ectoparasiticidal properties of the composition according the present invention alone (i.e. with no additional active ectoparasiticidal agent).

Ectoparasiticidal Tests Against Body Louse Eggs

Body louse eggs were obtained by providing actively laying adult lice with a close meshed nylon substrate, in place of the normal cotton corduroy substrate, over a 48 hour period. At the end of this period the insects were removed and the gauze cut into appropriately sized smaller pieces. The small gauze pieces were randomly allocated to plastic Petri dishes in advance of the test.

Each square of gauze with eggs on (4 cm$^2$) was then massaged with a close containing approximately 5 ml of the tested composition. This was performed on the dry gauze so that the products could be used neat and could be massaged in. Both the product and control were left on the gauze for the allotted exposure time of 60 minutes.

Gauze squares bearing the eggs were then incubated under normal maintenance conditions (30±2° C. and 50±15% relative humidity) for the remainder of the test period. At the end of exposure period the insects and gauze for the composition according to the present invention were rinsed using 500 ml of warm (35° C.) tap water poured through and over the gauze squares. They were then blotted dry using medical wipe tissue and incubated under normal maintenance conditions in clean plastic Petri dishes of the appropriate size until the results were recorded. The same testing procedure was applied for the comparative example.

Hedrin Once Spray Gel test gauzes bearing eggs were then shampooed off using a 1:14 frequent wash shampoo. They were then rinsed through using 500 ml of warm (35° C.) tap water poured through and over the gauze squares. They were then blotted dry using medical wipe tissue and incubated under normal maintenance conditions in clean plastic Petri dishes of the appropriate size until the results were recorded.

After the treatments had been washed off, the eggs were incubated at 25° C. and 75% relative humidity (RH) until all unaffected eggs had hatched between 10-14 days after testing. The eggs were then observed for their state of development.

Tests results are listed in Table III, wherein ectoparasiticidal has been calculated using the following egg development categories with regard to degree of penetration of the insecticide:

"Hatched": louse eggs that have not been penetrated by the insecticide so that the embryo inside the egg developed and hatched normally.

"Half-hatched": eggs penetrated by a small amount of insecticide, yet amount insufficient to kill the emerging insect prior hatching; or the emerging insect absorbed sufficient amount of insecticide from the outside of the eggshell to be killed it but only after it has partially emerged from the shell.

"Dead": eggs in which the embryo apparently completed its development but has not emerged from the eggshell, as well as eggs in which sufficient amount of insecticide was absorbed within outer layers of the eggshell between the chorionic membranes that surround the embryo and the eggshell cap, so that the insect was killed during hatching but before it was capable of lifting the lid from the eggshell.

"Undeveloped": eggs that failed to develop correctly or at all. This could be identified because at the time of testing the young embryos appear amorphous inside the transparent eggshell. When the developing embryo is about 48 hours old it starts to develop a small pigmented spot at the cap end of the shell. This spot will develop to become the eye of the louse and is referred to as the "eyespot". If a toxic material is capable of entering the eggshell and penetrating the chorionic membrane it can kill the young embryo before it has developed to the point of showing the eyespot. In some cases the embryo may develop only to the point of showing an eyespot but in these cases the spot is misshapen or may even be at the wrong end of the eggshell.

Percentage mortality has been calculated using the formula:

Mortality=(Half-hatched+Dead+Undeveloped)/(No of eggs in a sample)

TABLE III

Ectoparasiticidal properties of the composition according to the invention against body louse eggs compared to Hedrin Once Spray Gel and water control

| Formulation | Sample No | No of eggs in a sample | Hatched | Half-hatched | Dead | Undeveloped | Mortality [%] |
|---|---|---|---|---|---|---|---|
| Water (control) | 1. | 119 | 101 | 1 | 2 | 15 | |
| | 2. | 118 | 114 | 1 | 1 | 2 | |
| | 3. | 97 | 70 | 4 | 2 | 21 | |
| Total: | | 334 | 285 | 6 | 5 | 38 | 14.67 |
| Composition of the invention (Example 1) | 1 | 115 | 0 | 0 | 8 | 107 | |
| | 2 | 99 | 0 | 0 | 1 | 98 | |
| | 3 | 131 | 0 | 0 | 6 | 125 | |
| Total: | | 345 | 0 | 0 | 15 | 330 | 100.00 |

TABLE III-continued

Ectoparasiticidal properties of the composition according to the invention against body louse eggs compared to Hedrin Once Spray Gel and water control

| Formulation | Sample No | No of eggs in a sample | Hatched | Eggs Half-hatched | Dead | Undeveloped | Mortality [%] |
|---|---|---|---|---|---|---|---|
| Hedrin Once Spray Gel (Solpharm) | 1 | 111 | 1 | 0 | 0 | 110 | |
| | 2 | 106 | 1 | 0 | 0 | 105 | |
| | 3 | 106 | 2 | 0 | 0 | 104 | |
| Total: | | 323 | 4 | 0 | 0 | 319 | 98.76 |

As illustrated in Table III, the composition according to the present invention alone was unexpectedly the most effective (100% mortality) at killing louse eggs after a 60 minute exposure compared with Hedrin Spray Gel (98.76% mortality) and a water control (14.67% mortality).

Ectoparasiticidal Tests Against Adult Body Lice

Head lice, *Pediculus capitis*, were obtained from individual volunteers. On each day of testing all of the samples were evaluated once. For each of the tests performed on the same day all of the lice were obtained from the same individual patient so there was an internal consistency within a batch of test replicates. As only one replicate test of formulation was performed on any one day there could have been some variation between tests conducted on different days. However, this would have represented the normal variation of head lice likely to be encountered in the community and any variation of response would be representative of the range of response likely to be encountered in consumer use.

Lice were collected using plastic louse detection combs and transported to the laboratory within 2 hours. Lice were counted into batches that were provided with squares of nylon gauze, as a substrate upon which to stand, and each batch allocated to a marked 55 mm plastic Petri dish.

For the test procedure an aliquot of approximately 5-10 ml of the formulation was poured into the base of a clean 55 mm plastic Petri dish. The gauze bearing the lice was immersed in the fluid for 10 seconds, during which time the gauze was turned at least twice to ensure removal of air bubbles. After removal from the fluid the gauze and insects were lightly blotted to remove excess fluid and returned to a 5.5 mm marked Petri dish. The same procedure was repeated for the other replicate gauze squares in that batch.

Gauze squares bearing the lice were then incubated under normal maintenance conditions (30±2° C. and 50±15% relative humidity) for the remainder of the test period.

At the end of the 60 minutes exposure period, the insects and gauze were washed with water and then left for a further three minutes. They were then washed again using a bland toiletry shampoo diluted one part shampoo with fourteen parts water (FWS 1:15) after which they are rinsed using 500 ml of warm (35° C.) tap water poured through and over the gauze squares. They were then blotted dry using medical wipe tissue and incubated under normal maintenance conditions in clean plastic Petri dishes of the appropriate size until the results are recorded.

Tests results are listed in Table IV, wherein ectoparasiticidal activity has been calculated using the following lice categories:

"Immobile": louse shows no signs of movement; it is presumably dead.

"Moribund": louse retains some movement at the time the results are scored; such movements can range from complete physical immobility, with just small observable gut movements, through minor twitches of limbs, antennae or other appendages, to insects that are nearly able to crawl but are sufficiently lacking coordination, so that they could considered as incapable of continued survival; lice in this category were also classified in the overall mortality as being no longer effectively alive.

"Alive": louse appears to crawl normally and it is expected, given the opportunity to feed, to be able to live normally.

TABLE IV

Ectoparasiticidal properties of the composition according to the invention against head lice adults

| Formulation | Replicate | Total | Readings overnight after wash off | | | Mortality [%] |
|---|---|---|---|---|---|---|
| | | | Alive | Moribund | Immobile | |
| Composition of the invention (Example 1) | 1 | 15 | 0 | 0 | 15 | 100 |
| | 2 | 15 | 0 | 0 | 15 | 100 |
| Water (Control) | 1 | 15 | 15 | 0 | 0 | 0 |
| | 2 | 15 | 15 | 0 | 0 | 0 |

As illustrated in Table IV, the composition according to the present invention alone produces 100% efficacy against lice of mixed development stages when compared to water control. The overnight reading after 60 minutes exposure shows 100% mortality for the two test replicates with the controls all still alive.

Example 2

A composition of the present invention for combatting mammals ticks has been prepared containing:

isopropyl myristate (IPM) in the amount of 3.5% by weight;

isohexadecane in the amount of 1.5% by weight; and 1,1,1,2-tetrafluoroethane (HFC-134A) in the amount of 95% by weight as a spraying agent.

The composition has been sprayed directly on ticks attached to dog's skin. Ticks were frozen by the composition and simultaneously covered by the film containing IPM and isohexadecane spread over their bodies. Frozen ticks were then removed from the skin with tweezers. Removed ticks were dead, with no recovery effect observed (100% mortality). Positive control composition prepared pursuant to teachings of publication U.S. Pat. No. 4,834,967 (Example 1, a halogenated hydrocarbon aerosol refrigerant) showed over 20% of recovery after the treatment.

Example 3

A spot-on composition of the present invention with insect growth regulator (IGR) for controlling of fleas on cats has been prepared containing:
- isopropyl myristate (IPM) in the amount of 30.8% by weight;
- isohexadecane in the amount of 68% by weight;
- polyethylene glycol (30) hydroxystearate (as a surfactant) in the amount of 0.2% by weight; and
- pyriproxyfen (as an insect growth regulator) in the amount of 1% by weight.

The composition was applied in a dosage of 0.5 ml on skin of a cat and provided no adverse reaction based on cooling or sticky effect (it spreads easily and do not leave the skin greasy and sticky).

As shall be obvious to those skilled in the art all compositions of the present invention may be conveniently converted into a suitable dosage form together with at least one excipient or adjunct and, if appropriate, in combination with one or more additional active ingredients. The following dosage forms are therefore merely illustrative, and not limitative of the remainder of the disclosure in any way whatsoever.

Example A—Ampoules

Composition prepared according to Example 1 is filled into ampoules and the ampoules are sealed under sterile conditions. Each ampoule contains 20 ml of the composition. Ampoules may be used for a spot-on or pour-on treatment of pediculosis.

Example B—Aerosol

Composition prepared according to Example 1 is filed into a pressurised container with a suitable propellant (e.g. propane-butane dichlorodifluoromethane, trichlorofluoromethane, dichlorotetrafluoroethane, carbon dioxide or other suitable gas). Such a dosage unit may be additionally provided with a valve to deliver a predetermined amount.

Example C—Sprayer

Composition prepared according to Example 1 is filed into a container of a hand-pumped sprayer provided with a nozzle.

All the above embodiments of the present invention are merely exemplary. These and other factors, however, should not be considered as limiting the spirit of the invention, the intended scope of protection of which is indicated in appended claims.

The invention claimed is:
1. An insecticidal composition for combating ectoparasites comprising:
   an ectoparasiticidal liquid spreading composition comprising between 3.5% and 50% by weight isopropyl myristate and between 1.5% and 68% by weight isohexadecane, and
   a spraying agent;
   wherein the ectoparasiticidal liquid spreading composition does not comprise silicones.
2. The composition according to claim 1, wherein the ectoparasiticidal liquid spreading composition further comprises at least one surfactant in an amount of up to 10% by weight.
3. The composition according to claim 1, wherein the ectoparasiticidal liquid spreading composition further comprises at least one additional agent selected from the group consisting of an inert pharmaceutically or cosmetically acceptable carrier, fragrance, insecticide, or insect growth regulator.
4. The composition according to claim 1, wherein the ectoparasiticidal liquid spreading composition further comprises at least one additional agent selected from the group consisting of an insecticide and an insect growth regulator.

* * * * *